US006248533B1

(12) United States Patent
Kamizono et al.

(10) Patent No.: US 6,248,533 B1
(45) Date of Patent: Jun. 19, 2001

(54) GENE DIAGNOSIS OF DISEASES WHEREIN TNF-α PROMOTORS PARTICIPATE

(75) Inventors: Shintaro Kamizono; Akira Yamada; Takafumi Higuchi; Hirohisa Kato, all of Fukuoka; Kyogo Itoh, Saga; Naoko Seki, Fukuoka, all of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/448,176

(22) Filed: Nov. 24, 1999

Related U.S. Application Data

(63) Continuation-in-part of application No. PCT/JP97/04304, filed on Nov. 26, 1997, and a continuation-in-part of application No. PCT/JP98/02270, filed on May 25, 1998.

(30) Foreign Application Priority Data

May 26, 1997 (JP) .................................................... 9-134973
Jun. 30, 1997 (JP) .................................................... 9-173900

(51) Int. Cl.[7] .............................. C07H 21/04; C12Q 1/68
(52) U.S. Cl. ................................. 435/6; 536/23.1
(58) Field of Search ................................ 435/6; 536/23.1

(56) References Cited

PUBLICATIONS

Kamizono et al "Susceptible locus for obese type II diabetes mellitus in the 5' flanking region of the tumor necrosis factor–alpha–gene" Tissue Antigens, vol. 55, p. 449–452, May 2000.*

Seki et al "Polymorphisms in the 5'-flanking region of tumor necrosis factor–alpha–gene in patients with rheumatoid arthritis" Tissue Antigens, vol. 54, p. 194–197, Aug. 1999.*

Higuchi et al "Polymorhpism of the 5' flanking region of the human tumor necrosis factor (TNF)–alpha–gene in Japanese" Tissue Antigens, vol. 51, pp. 605–612, Jun. 1998.*

Deng et al "No primary association between the 308 polymorphism in the tumor necrosis factor alpha promoter region and IDDM" Human Immunology, vol. 45, p. 137–142, Feb. 1996.*

Huizinga et al "Disease susceptibility related to the –238 TNF alpha G to A promoter polymorphism" European Cytokine Network, vol. 7, No. 2, pp. 259, 1996.*

Shogo Takashiba et al., "Cloning and characterization of human TNFα promoter region.", Gene, vol. 131, pp. 307–308, 1993.

J. Vinasco et al., "Polymorphism at the TNF loci in rheumatoid arthritis.", Tissue Antigens, vol. 49, pp. 74–78, 1997.

C.P. Day et al., "Tumour necrosis factor–alpha gene promoter polymorphism and decreased insulin resistance.", Diabetologia, vol. 41, pp. 430–434, 1998.

H. Rothe et al., "Abnormal TNF production in prediabetic BB rats is linked to defective CD45R exxpression.", Immunology, vol. 77, pp. 1–6, 1992.

Takafumi Higuti et al., "Relationship between polymorphism of TNF–alpha gene promoter region and ability to produce TNF–alpha .", Presentation, Japan Immunology Society, Pacifico Yokohama Meeting Center, Nov. 27, 1996, 19 pages, Certification, 2 pages.

* cited by examiner

*Primary Examiner*—Lisa B. Arthur
*Assistant Examiner*—Jeanine Goldberg
(74) *Attorney, Agent, or Firm*—Foley & Lardner

(57) ABSTRACT

A method of gene diagnosis of diseases wherein TNF-α promoters participate, such as juvenile rheumatoid arthritis, chronic rheumatism or diabetes, by determining in the nucleotides at the −857, −863 and/or −1031 positions in the 5'-flanking region of a TNF-α gene.

4 Claims, 9 Drawing Sheets

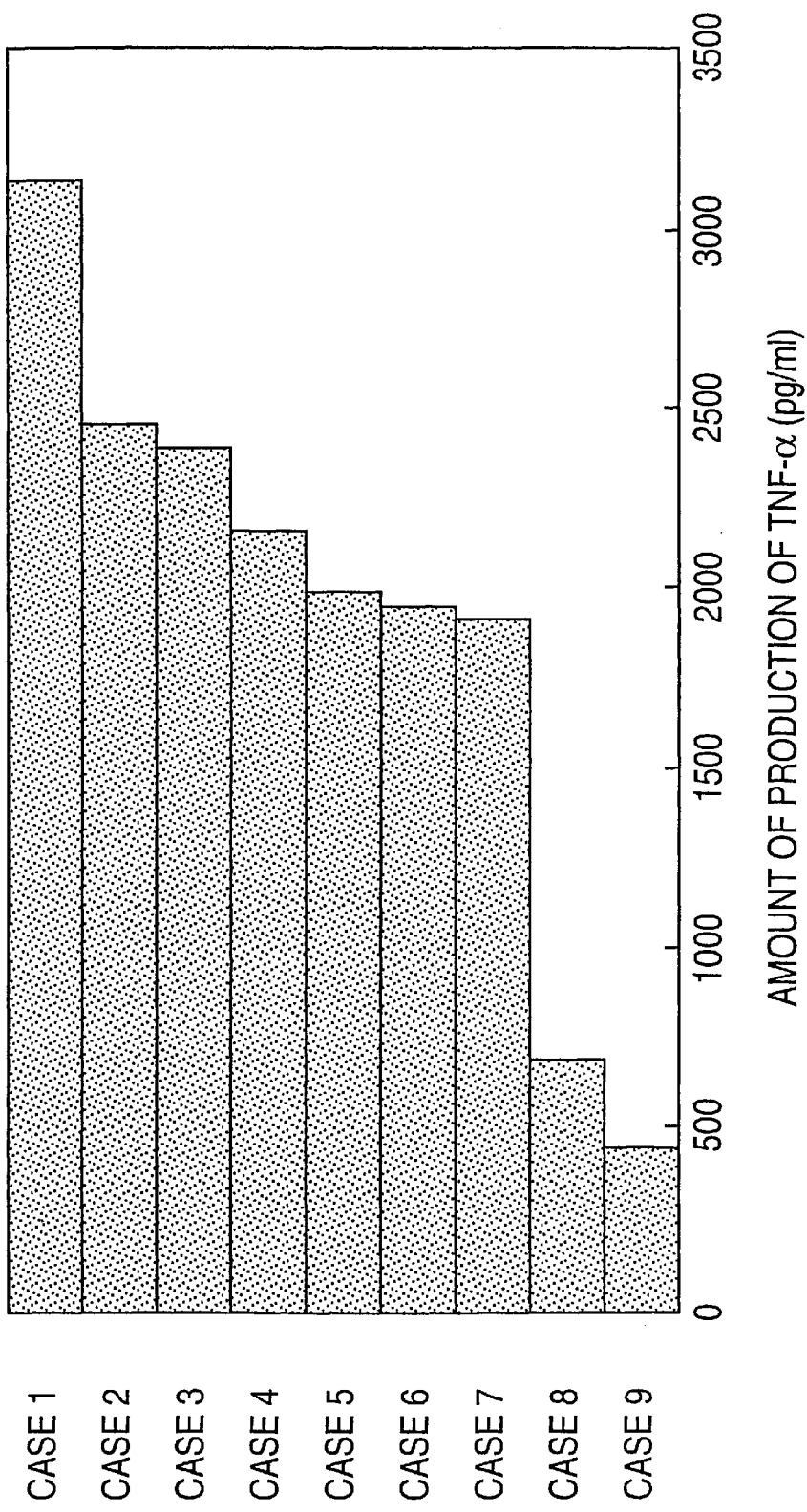

FIG. 2 POLYMORPHISMS IN TNF-α GENE PROMOTER REGION

| HEALTHY DONOR | HLA/DRB1* | AMOUNT OF PRODUCTION OF TNF-α | PRESERVED SEQUENCE | POSITION FROM THE TRANSCRIPTION INITIATION POINT OF TNF-α GENE | | |
|---|---|---|---|---|---|---|
| | | | | -1031 | -863 | -857 |
| | | | | T | C | C |
| CASE 1 | 04051/1502 | HIGH | X | T | C | T |
| | | | Y | T | C | C |
| CASE 2 | 0405/0901 | HIGH | X | T | C | T |
| | | | Y | C | A | C |
| CASE 3 | 0101/1501 | HIGH | X | T | C | C |
| | | | Y | C | A | C |
| CASE 4 | 1501/1602 | HIGH | X | T | C | C |
| | | | Y | T | C | C |
| CASE 5 | 0802/1201 | HIGH | X | T | C | C |
| | | | Y | C | A | C |
| CASE 6 | 04051/1502 | HIGH | X | T | C | T |
| | | | Y | T | C | C |
| CASE 7 | 0901/1501 | HIGH | X | T | C | C |
| | | | Y | T | C | C |
| CASE 8 | 04051/0901 | LOW | X | T | C | C |
| | | | Y | T | C | C |
| CASE 9 | 1101/1302 | LOW | X | T | C | C |
| | | | Y | T | C | C |

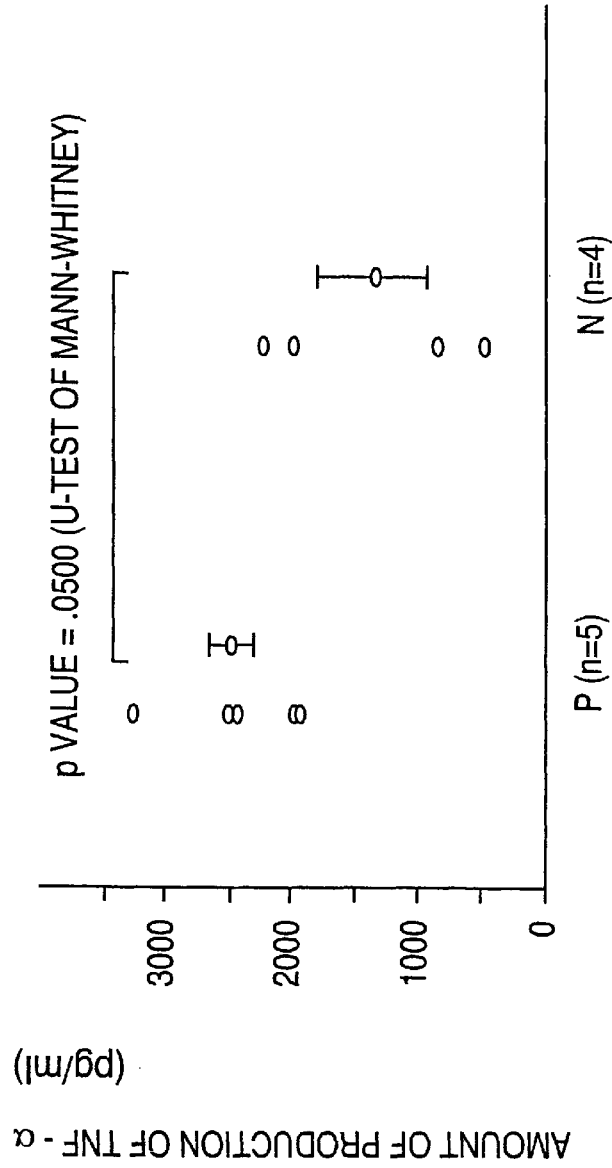

ASO-Hybridization analysis of TNF-α promoter region

FIG. 7a

```
TNF-alpha(consensus)  GCTTGTGTGT GTGTGTCTGG GAGTGAGAAC TTCCCAGTCT ATCTAAGGAA TGGAGGGAGG   60
TNF-alpha(case2-X)    GCTTGTGTGT GTGTGTCTGG GAGTGAGAAC TTCCCAGTCT ATCTAAGGAA TGGAGGGAGG   60
TNF-alpha(case2-Y)    GCTTGTGTGT GTGTGTCTGG GAGTGAGAAC TTCCCAGTCT ATCTAAGGAA TGGAGGGAGG   60

TNF-alpha(consensus)  GACAGAGGGC TCAAAGGGAG CAAGAGCTGT GGGGAGAACA AAAGGATAAG GGCTCAGAGA  120
TNF-alpha(case2-X)    GACAGAGGGC TCAAAGGGAG CAAGAGCTGT GGGGAGAACA AAAGGATAAG GGCTCAGAGA  120
TNF-alpha(case2-Y)    GACAGAGGGC TCAAAGGGAG CAAGAGCTGT GGGGAGAACA AAAGGATAAG GGCTCAGAGA  120

TNF-alpha(consensus)  GCTTCAGGGA TATGTGATGG ACTCACCAGG TGAGGCCGCC AGACTGCTGC AGGGGAAGCA  180
TNF-alpha(case2-X)    GCTTCAGGGA TATGTGATGG ACTCACCAGG TGAGGCCGCC AGACTGCTGC AGGGGAAGCA  180
TNF-alpha(case2-Y)    GCTTCAGGGA TATGTGATGG ACTCACCAGG TGAGGCCGCC AGACTGCTGC AGGGGAAGCA  180
                                           -1091
                                             ↓
TNF-alpha(consensus)  AAGGAGAAGC TGAGAAGAATG AAGGAAAAGT CAGGGTCTGG AGGGGCGGGG GTCAGGGAGC  240
TNF-alpha(case2-X)    AAGGAGAAGC TGAGAAGATG AAGGAAAAGT CAGGGTCTGG AGGGGCGGGG GTCAGGGAGC  240
TNF-alpha(case2-Y)    AAGGAGAAGC TGAGAAGACG AAGGAAAAGT CAGGGTCTGG AGGGGCGGGG GTCAGGGAGC  240

TNF-alpha(consensus)  TCCTGGGAGA TATGGCCACA TGTAGCGGCT CTGAGGAATG GGTTACAGGA GACCTCTGGG  300
TNF-alpha(case2-X)    TCCTGGGAGA TATGGCCACA TGTAGCGGCT CTGAGGAATG GGTTACAGGA GACCTCTGGG  300
TNF-alpha(case2-Y)    TCCTGGGAGA TATGGCCACA TGTAGCGGCT CTGAGGAATG GGTTACAGGA GACCTCTGGG  300

TNF-alpha(consensus)  GAGATGTGAC CACAGCAATG GGTAGGAGAA TGTCCAGGGC TATGGAAGTC GAGTATGGGG  360
TNF-alpha(case2-X)    GAGATGTGAC CACAGCAATG GGTAGGAGAA TGTCCAGGGC TATGGAAGTC GAGTATGGGG  360
TNF-alpha(case2-Y)    GAGATGTGAC CACAGCAATG GGTAGGAGAA TGTCCAGGGC TATGGAAGTC GAGTATGGGG  360
                       -863
                         ↓
TNF-alpha(consensus)  ACCCCCCTT  AACGAAGACA GGGCCATGTA GAGGGCCCCA GGGAGTGAAA GAGCCTCCAG  420
TNF-alpha(case2-X)    ACCCCCCTT  AATGAAGACA GGGCCATGTA GAGGGCCCCA GGGAGTGAAA GAGCCTCCAG  420
TNF-alpha(case2-Y)    ACCCCCACTT AACGAAGACA GGGCCATGTA GAGGGCCCCA GGGAGTGAAA GAGCCTCCAG  420
                       -857
                         ↓
TNF-alpha(consensus)  GACCTCCAGG TATGGAATAC AGGGGACGTT TAAGAAGATA TGGCCACACA CTGGGGCCCT  480
TNF-alpha(case2-X)    GACCTCCAGG TATGGAATAC AGGGGACGTT TAAGAAGATA TGGCCACACA CTGGGGCCCT  480
TNF-alpha(case2-Y)    GACCTCCAGG TATGGAATAC AGGGGACGTT TAAGAAGATA TGGCCACACA CTGGGGCCCT  480
```

FIG. 7b

```
TNF-alpha(consensus)  GAGAAGTGAG AGCTTCATGA AAAAAATCAG GGACCCCAGA GTTCCTTGGA AGCCAAGACT  540
TNF-alpha(case2-X)    GAGAAGTGAG AGCTTCATGA AAAAAATCAG GGACCCCAGA GTTCCTTGGA AGCCAAGACT  540
TNF-alpha(case2-Y)    GAGAAGTGAG AGCTTCATGA AAAAAATCAG GGACCCCAGA GTTCCTTGGA AGCCAAGACT  540

TNF-alpha(consensus)  GAAACCAGCA TTATGAGTCT CCGGGTCAGA ATGAAAGAAG AAGGCCTGCC CCAGTGGGGT  600
TNF-alpha(case2-X)    GAAACCAGCA TTATGAGTCT CCGGGTCAGA ATGAAAGAAG AAGGCCTGCC CCAGTGGGGT  600
TNF-alpha(case2-Y)    GAAACCAGCA TTATGAGTCT CCGGGTCAGA ATGAAAGAAG AAGGCCTGCC CCAGTGGGGT  600

TNF-alpha(consensus)  CTGTGAATTC CCGGGGGTGA TTTCACTCCC CGGGGCTGTC CCAGGCTTGT CCCTGCTACC  660
TNF-alpha(case2-X)    CTGTGAATTC CCGGGGGTGA TTTCACTCCC CGGGGCTGTC CCAGGCTTGT CCCTGCTACC  660
TNF-alpha(case2-Y)    CTGTGAATTC CCGGGGGTGA TTTCACTCCC CGGGGCTGTC CCAGGCTTGT CCCTGCTACC  660

TNF-alpha(consensus)  CCCACCCAGC CTTTCCTGAG GCCTCAAGCC TGCCACCAAG CCCCCAGCTC CTTCTCCCCG  720
TNF-alpha(case2-X)    CCCACCCAGC CTTTCCTGAG GCCTCAAGCC TGCCACCAAG CCCCCAGCTC CTTCTCCCCG  720
TNF-alpha(case2-Y)    CCCACCCAGC CTTTCCTGAG GCCTCAAGCC TGCCACCAAG CCCCCAGCTC CTTCTCCCCG  720

TNF-alpha(consensus)  CAGGGACCCA AACACAGGCC TCAGGACTCA ACACAGCTTT TCCCTCCAAC CCCGTTTTCT  780
TNF-alpha(case2-X)    CAGGGACCCA AACACAGGCC TCAGGACTCA ACACAGCTTT TCCCTCCAAC CCCGTTTTCT  780
TNF-alpha(case2-Y)    CAGGGACCCA AACACAGGCC TCAGGACTCA ACACAGCTTT TCCCTCCAAC CCCGTTTTCT  780

TNF-alpha(consensus)  CTCCCTCAAG GACTCAGCTT TCTGAAGCCC CTCCCAGTTC TAGTTCTATC TTTTTCCTGC  840
TNF-alpha(case2-X)    CTCCCTCAAG GACTCAGCTT TCTGAAGCCC CTCCCAGTTC TAGTTCTATC TTTTTCCTGC  840
TNF-alpha(case2-Y)    CTCCCTCAAG GACTCAGCTT TCTGAAGCCC CTCCCAGTTC TAGTTCTATC TTTTTCCTGC  840

TNF-alpha(consensus)  ATCCTGTCTG GAAGTTAGAA GGAAACAGAC CACAGACCTG GTCCCAAAA  GAAATGGAGG  900
TNF-alpha(case2-X)    ATCCTGTCTG GAAGTTAGAA GGAAACAGAC CACAGACCTG GTCCCAAAA  GAAATGGAGG  900
TNF-alpha(case2-Y)    ATCCTGTCTG GAAGTTAGAA GGAAACAGAC CACAGACCTG GTCCCCAAAA GAAATGGAGG  900

TNF-alpha(consensus)  CAATAGGTTT TGAGGGGCAT GGGGACGGGG TTCAGCCTCC AGGGTCCTAC ACACAAATCA  960
TNF-alpha(case2-X)    CAATAGGTTT TGAGGGGCAT GGGGACGGGG TTCAGCCTCC AGGGTCCTAC ACACAAATCA  960
TNF-alpha(case2-Y)    CAATAGGTTT TGAGGGGCAT GGGGACGGGG TTCAGCCTCC AGGGTCCTAC ACACAAATCA  960
```

FIG. 7c

| | | | | | | | |
|---|---|---|---|---|---|---|---|
| TNF-alpha(consensus) | GTCAGTGGCC | CAGAAGACCC | CCCTCGGAAT | CGGAGCAGGG | AGGATGGGGA | GTGTGAGGGG | 1020 |
| TNF-alpha(case2-X) | GTCAGTGGCC | CAGAAGACCC | CCCTCGGAAT | CGGAGCAGGG | AGGATGGGGA | GTGTGAGGGG | 1020 |
| TNF-alpha(case2-Y) | GTCAGTGGCC | CAGAAGACCC | CCCTCGGAAT | CGGAGCAGGG | AGGATGGGGA | GTGTGAGGGG | 1020 |
| TNF-alpha(consensus) | TATCCTTGAT | GCTTGTGTGT | CCCCAACTTT | CCAAATCCCC | GCCCCCGCGA | TGGAGAAGAA | 1080 |
| TNF-alpha(case2-X) | TATCCTTGAT | GCTTGTGTGT | CCCCAACTTT | CCAAATCCCC | GCCCCCGCGA | TGGAGAAGAA | 1080 |
| TNF-alpha(case2-Y) | TATCCTTGAT | GCTTGTGTGT | CCCCAACTTT | CCAAATCCCC | GCCCCCGCGA | TGGAGAAGAA | 1080 |
| TNF-alpha(consensus) | ACCGAGACAG | AAGGTGCAGG | GCCCACTACC | GCTTCCTCCA | GATGAGCTCA | TGGGTTTCTC | 1140 |
| TNF-alpha(case2-X) | ACCGAGACAG | AAGGTGCAGG | GCCCACTACC | GCTTCCTCCA | GATGAGCTCA | TGGGTTTCTC | 1140 |
| TNF-alpha(case2-Y) | ACCGAGACAG | AAGGTGCAGG | GCCCACTACC | GCTTCCTCCA | GATGAGCTCA | TGGGTTTCTC | 1140 |
| TNF-alpha(consensus) | CACCAAGGAA | GTTTTCCGCT | GGTTGAATGA | TTCTTTCCCC | GCCCTCCTCT | CGCCCCAGGG | 1200 |
| TNF-alpha(case2-X) | CACCAAGGAA | GTTTTCCGCT | GGTTGAATGA | TTCTTTCCCC | GCCCTCCTCT | CGCCCCAGGG | 1200 |
| TNF-alpha(case2-Y) | CACCAAGGAA | GTTTTCCGCT | GGTTGAATGA | TTCTTTCCCC | GCCCTCCTCT | CGCCCCAGGG | 1200 |
| TNF-alpha(consensus) | ACATATAAAG | GCAGTTGTTG | GCACACCCA | CCAGCAGACG | CTCCCTCAGC | AAGGACAGCA | 1260 |
| TNF-alpha(case2-X) | ACATATAAAG | GCAGTTGTTG | GCACACCCA | CCAGCAGACG | CTCCCTCAGC | AAGGACAGCA | 1260 |
| TNF-alpha(case2-Y) | ACATATAAAG | GCAGTTGTTG | GCACACCCA | CCAGCAGACG | CTCCCTCAGC | AAGGACAGCA | 1260 |
| TNF-alpha(consensus) | GAGGACCAGC | TAAGAGGGAG | AGAAGCAACT | ACAGACCCCC | CCTGAAAACA | ACCCTCAGAC | 1320 |
| TNF-alpha(case2-X) | GAGGACCAGC | TAAGAGGGAG | AGAAGCAACT | ACAGACCCCC | CCTGAAAACA | ACCCTCAGAC | 1320 |
| TNF-alpha(case2-Y) | GAGGACCAGC | TAAGAGGGAG | AGAAGCAACT | ACAGACCCCC | CCTGAAAACA | ACCCTCAGAC | 1320 |
| TNF-alpha(consensus) | GCCACATCCC | CTGACAAGCT | GCCAGGCAGG | TTCTCTT | | | 1357 |
| TNF-alpha(case2-X) | GCCACATCCC | CTGACAAGCT | GCCAGGCAGG | TTCTCTT | | | 1357 |
| TNF-alpha(case2-Y) | GCCACATCCC | CTGACAAGCT | GCCAGGCAGG | TTCTCTT | | | 1357 |

```
                        SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Primer"

(xi) SEQUENCE DESCRIPTION: SEQ ID NO: 1:

GCTTGTGTGT GTGTGTCTGG                                                 20

(2) INFORMATION FOR SEQ ID NO: 2:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Primer"

(xi) SEQUENCE DESCRIPTION: SEQ ID NO: 2:

GGACACACAA GCATCAAGG                                                  19

(2) INFORMATION FOR SEQ ID NO: 3:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Allele specific (xi) SEQUENCE DESCRIPTION: SEQ ID NO: 3:

CTTAACGAAG ACAGGGCC                                                   18

(2) INFORMATION FOR SEQ ID NO: 4:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Allele specific (xi) SEQUENCE DESCRIPTION: SEQ ID NO: 4:

CTTAATGAAG ACAGGGCC                                                   18
```

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Allele specific (xi) SEQUENCE DESCRIPTION: SEQ ID NO: 5:

ATGGGGACCC CCCCTTAA                                              18

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Allele specific (xi) SEQUENCE DESCRIPTION: SEQ ID NO: 6:

ATGGGGACCC CCACTTAA                                              18

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Allele specific (xi) SEQUENCE DESCRIPTION: SEQ ID NO: 7:

CTGAGAAGAT GAAGGAAA                                              18

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Allele specific (xi) SEQUENCE DESCRIPTION: SEQ ID NO: 8:

CTGAGAAGAC GAAGGAAA                                              18

(2) INFORMATION FOR SEQ ID NO: 9:

(i) SEQUENCE CHARACTERISTICS:
        (A) LENGTH: 1357 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 9:

GCTTGTGTGT GTGTGTCTGG GAGTGAGAAC TTCCCAGTCT ATCTAAGGAA TGGAGGGAGG    60

```
GACAGAGGGC TCAAAGGGAG CAAGAGCTGT GGGGAGAACA AAAGGATAAG GGCTCAGAGA         120

GCTTCAGGGA TATGTGATGG ACTCACCAGG TGAGGCCGCC AGACTGCTGC AGGGGAAGCA         180

AAGGAGAAGC TGAGAAGATG AAGGAAAAGT CAGGGTCTGG AGGGGCGGGG GTCAGGGAGC         240

TCCTGGGAGA TATGGCCACA TGTAGCGGCT CTGAGGAATG GGTTACAGGA GACCTCTGGG         300

GAGATGTGAC CACAGCAATG GGTAGGAGAA TGTCCAGGGC TATGGAAGTC GAGTATGGGG         360

ACCCCCCCTT AACGAAGACA GGGCCATGTA GAGGGCCCCA GGGAGTGAAA GAGCCTCCAG         420

GACCTCCAGG TATGGAATAC AGGGGACGTT TAAGAAGATA TGGCCACACA CTGGGCCCT         480

GAGAAGTGAG AGCTTCATGA AAAAAATCAG GGACCCCAGA GTTCCTTGGA AGCCAAGACT         540

GAAACCAGCA TTATGAGTCT CCGGGTCAGA ATGAAAGAAG AAGGCCTGCC CCAGTGGGGT         600

CTGTGAATTC CCGGGGGTGA TTTCACTCCC CGGGGCTGTC CCAGGCTTGT CCCTGCTACC         660

CCCACCCAGC CTTTCCTGAG GCCTCAAGCC TGCCACCAAG CCCCCAGCTC CTTCTCCCCG         720

CAGGGACCCA ACACAGGCC TCAGGACTCA ACACAGCTTT TCCCTCCAAC CCCGTTTTCT         780

CTCCCTCAAG GACTCAGCTT TCTGAAGCCC CTCCCAGTTC TAGTTCTATC TTTTTCCTGC         840

ATCCTGTCTG GAAGTTAGAA GGAAACAGAC CACAGACCTG GTCCCCAAAA GAAATGGAGG         900

CAATAGGTTT TGAGGGGCAT GGGGACGGGG TTCAGCCTCC AGGGTCCTAC ACACAAATCA         960

GTCAGTGGCC CAGAAGACCC CCCTCGGAAT CGGAGCAGGG AGGATGGGGA GTGTGAGGGG        1020

TATCCTTGAT GCTTGTGTGT CCCCAACTTT CCAAATCCCC GCCCCCGCGA TGGAGAAGAA        1080

ACCGAGACAG AAGGTGCAGG GCCCACTACC GCTTCCTCCA GATGAGCTCA TGGGTTTCTC        1140

CACCAAGGAA GTTTTCCGCT GGTTGAATGA TTCTTTCCCC GCCCTCCTCT CGCCCCAGGG        1200

ACATATAAAG GCAGTTGTTG GCACACCCAG CCAGCAGACG CTCCCTCAGC AAGGACAGCA        1260

GAGGACCAGC TAAGAGGGAG AGAAGCAACT ACAGACCCCC CCTGAAAACA ACCCTCAGAC        1320

GCCACATCCC CTGACAAGCT GCCAGGCAGG TTCTCTT                                1357

(2) INFORMATION FOR SEQ ID NO: 10:

(i) SEQUENCE CHARACTERISTICS:
            (A) LENGTH: 1357 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 10:

GCTTGTGTGT GTGTGTCTGG GAGTGAGAAC TTCCCAGTCT ATCTAAGGAA TGGAGGGAGG          60

GACAGAGGGC TCAAAGGGAG CAAGAGCTGT GGGGAGAACA AAAGGATAAG GGCTCAGAGA         120

GCTTCAGGGA TATGTGATGG ACTCACCAGG TGAGGCCGCC AGACTGCTGC AGGGGAAGCA         180

AAGGAGAAGC TGAGAAGATG AAGGAAAAGT CAGGGTCTGG AGGGGCGGGG GTCAGGGAGC         240

TCCTGGGAGA TATGGCCACA TGTAGCGGCT CTGAGGAATG GGTTACAGGA GACCTCTGGG         300

GAGATGTGAC CACAGCAATG GGTAGGAGAA TGTCCAGGGC TATGGAAGTC GAGTATGGGG         360

ACCCCCCCTT AATGAAGACA GGGCCATGTA GAGGGCCCCA GGGAGTGAAA GAGCCTCCAG         420

GACCTCCAGG TATGGAATAC AGGGGACGTT TAAGAAGATA TGGCCACACA CTGGGCCCT         480

GAGAAGTGAG AGCTTCATGA AAAAAATCAG GGACCCCAGA GTTCCTTGGA AGCCAAGACT         540

GAAACCAGCA TTATGAGTCT CCGGGTCAGA ATGAAAGAAG AAGGCCTGCC CCAGTGGGGT         600

CTGTGAATTC CCGGGGGTGA TTTCACTCCC CGGGGCTGTC CCAGGCTTGT CCCTGCTACC         660
```

```
CCCACCCAGC CTTTCCTGAG GCCTCAAGCC TGCCACCAAG CCCCCAGCTC CTTCTCCCCG        720

CAGGGACCCA AACACAGGCC TCAGGACTCA ACACAGCTTT TCCCTCCAAC CCCGTTTTCT        780

CTCCCTCAAG GACTCAGCTT TCTGAAGCCC CTCCCAGTTC TAGTTCTATC TTTTTCCTGC        840

ATCCTGTCTG GAAGTTAGAA GGAAACAGAC CACAGACCTG GTCCCAAAAA GAAATGGAGG        900

CAATAGGTTT TGAGGGGCAT GGGGACGGGG TTCAGCCTCC AGGGTCCTAC ACACAAATCA        960

GTCAGTGGCC CAGAAGACCC CCCTCGGAAT CGGAGCAGGG AGGATGGGGA GTGTGAGGGG       1020

TATCCTTGAT GCTTGTGTGT CCCCAACTTT CCAAATCCCC GCCCCGCGA TGGAGAAGAA        1080

ACCGAGACAG AAGGTGCAGG GCCCACTACC GCTTCCTCCA GATGAGCTCA TGGGTTTCTC       1140

CACCAAGGAA GTTTTCCGCT GGTTGAATGA TTCTTTCCCC GCCCTCCTCT CGCCCCAGGG       1200

ACATATAAAG GCAGTTGTTG GCACACCCAG CCAGCAGACG CTCCCTCAGC AAGGACAGCA       1260

GAGGACCAGC TAAGAGGGAG AGAAGCAACT ACAGACCCCC CCTGAAAACA ACCCTCAGAC       1320

GCCACATCCC CTGACAAGCT GCCAGGCAGG TTCTCTT                                1357

(2) INFORMATION FOR SEQ ID NO: 11:

(i) SEQUENCE CHARACTERISTICS:
        (A) LENGTH: 1357 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 11:

GCTTGTGTGT GTGTGTCTGG GAGTGAGAAC TTCCCAGTCT ATCTAAGGAA TGGAGGGAGG         60

GACAGAGGGC TCAAAGGGAG CAAGAGCTGT GGGGAGAACA AAAGGATAAG GGCTCAGAGA        120

GCTTCAGGGA TATGTGATGG ACTCACCAGG TGAGGCCGCC AGACTGCTGC AGGGGAAGCA        180

AAGGAGAAGC TGAGAAGACG AAGGAAAAGT CAGGGTCTGG AGGGGCGGGG GTCAGGGAGC        240

TCCTGGGAGA TATGGCCACA TGTAGCGGCT CTGAGGAATG GGTTACAGGA GACCTCTGGG        300

GAGATGTGAC CACAGCAATG GGTAGGAGAA TGTCCAGGGC TATGGAAGTC GAGTATGGGG        360

ACCCCCACTT AACGAAGACA GGGCCATGTA GAGGGCCCCA GGGAGTGAAA GAGCCTCCAG        420

GACCTCCAGG TATGGAATAC AGGGGACGTT TAAGAAGATA TGGCCACACA CTGGGGCCCT        480

GAGAAGTGAG AGCTTCATGA AAAAAATCAG GGACCCCAGA GTTCCTTGGA AGCCAAGACT        540

GAAACCAGCA TTATGAGTCT CCGGGTCAGA ATGAAAGAAG AAGGCCTGCC CCAGTGGGGT        600

CTGTGAATTC CCGGGGGTGA TTTCACTCCC CGGGGCTGTC CCAGGCTTGT CCCTGCTACC        660

CCCACCCAGC CTTTCCTGAG GCCTCAAGCC TGCCACCAAG CCCCCAGCTC CTTCTCCCCG        720

CAGGGACCCA AACACAGGCC TCAGGACTCA ACACAGCTTT TCCCTCCAAC CCCGTTTTCT        780

CTCCCTCAAG GACTCAGCTT TCTGAAGCCC CTCCCAGTTC TAGTTCTATC TTTTTCCTGC        840

ATCCTGTCTG GAAGTTAGAA GGAAACAGAC CACAGACCTG GTCCCAAAAA GAAATGGAGG        900

CAATAGGTTT TGAGGGGCAT GGGGACGGGG TTCAGCCTCC AGGGTCCTAC ACACAAATCA        960

GTCAGTGGCC CAGAAGACCC CCCTCGGAAT CGGAGCAGGG AGGATGGGGA GTGTGAGGGG       1020

TATCCTTGAT GCTTGTGTGT CCCCAACTTT CCAAATCCCC GCCCCGCGA TGGAGAAGAA        1080

ACCGAGACAG AAGGTGCAGG GCCCACTACC GCTTCCTCCA GATGAGCTCA TGGGTTTCTC       1140

CACCAAGGAA GTTTTCCGCT GGTTGAATGA TTCTTTCCCC GCCCTCCTCT CGCCCCAGGG       1200

ACATATAAAG GCAGTTGTTG GCACACCCAG CCAGCAGACG CTCCCTCAGC AAGGACAGCA       1260
```

| | |
|---|---|
| GAGGACCAGC TAAGAGGGAG AGAAGCAACT ACAGACCCCC CCTGAAAACA ACCCTCAGAC | 1320 |
| GCCACATCCC CTGACAAGCT GCCAGGCAGG TTCTCTT | 1357 |

GENE DIAGNOSIS OF DISEASES WHEREIN TNF-α PROMOTORS PARTICIPATE

This is a continuation-in-part application of PCT applications No. PCT/JP97/04304 filed on Nov. 26, 1997 and PCT/JP98/02270 filed on May 25, 1998.

TECHNICAL FIELD

The present invention relates t o genetic diagnosis, and in particular, to genetic diagnosis of diseases wherein tumor necrosis factor-α (hereinafter referred to as TNF-α) participates.

BACKGROUND ART

TNF-α is a protein which is produced from certain cells, including, for example, T cells, macrophages, and natural killer cells, by induction with prophlogistic agents such as bacteria, viruses, various mitogens or the like, and has the biological activities as described below:

1) a factor inducing hemorrhagic necrosis in tumors (in vivo),
2) induction of apoptosis in cancer cells (in vitro),
3) production of prostaglandins and collagenase,
4) expression of adhesion molecules (ICAM-1, ELAM-1),
5) expression of HLA class II,
6) production of inflammatory cytokines (IL-1, IL-6),
7) production of chemokines (IL-8, RANTES), and
8) enhancement of absorption of bone and cartilage.

TNF-α is believed to be an important agent that is located at most upstream in pathogenetic cytokine cascades of various inflammatory diseases.

Individual differences in amount of production of TNF-α have been previously pointed out. In addition, TNF-α is an important cytokine that is involved in vascular disorders. In the acute phase of Kawasaki disease, TNF-α exhibits an abnormally high level in serum, and it is said that the amount of production of TNF-α is enhanced in peripheral blood monocytes in this phase. These facts suggest that TNF-α plays an important role in onset of Kawasaki diseases of which major lesion is systemic vascular disorders (M. Sakaguchi, H. Kato, A. Nishiyori, K. Sagawa and K. Itho, *Production of tumor necrosis factor-alpha by Vβ$^{2-}$ or Vβ8$^-$ CD4$^+$ T cells in Kawasaki disease* in "Kawasaki disease" (H. Kato, Ed.), pp. 206–213, Elsevier, Amsterdam (1995)). It is thus expected that increased amount of TNF-α production based on genetic factors may be involved in onset and severity of Kawasaki disease.

Similarly, production of TNF-α is also enhanced in rheumatism (M. Sebbag, S. L. Parry, F. M. Brennan and M. Feldmann, "Cytokine stimulation of T lymphocytes regulates their capacity to induce monocyte production of tumor necrosis factor-alpha, but not interleukin-10: possible relevance to pathophysiology of rheumatoid arthritis", *Eur. J. Immunol.* 27:624–632 (1997)).

On the contrary, the capacity to produce TNF is said to be low in SLE nephropathy (C. 0. Jacob, Z. Fronek, G. D. Lewis, M. Koo, J. A. Hansen and H. 0. McDevitt, "Heritable major histocompatibility complex class II-associated differences in production of tumor necrosis factor c: Relevance to genetic predisposition to systemic lupus erythematosusf *Proc. Natl. Acad. Si. USA,* 87:1233–1237 (1990)).

DISCLOSURE OF THE INVENTION

It is thus expected that onset and severity of certain diseases may be related to the capacity of the individual to produce TNF-α.

Therefore, if one can objectively measure the capacity of a given individual to produce TNF-α based on genetic factors, prior diagnosis (liability to a disease, severity upon onset of the disease, reactivity to treatments) or de termination of prognosis of diseases wherein TNF-α participates can be conducted.

To attain such an object, the present inventors extensively studied. In result, the present inventors have found that there exists genetic polymorphisms of nucleotide changes in the 5'-flanking (promoter) region of TNF-α gene, and that said nucleotide changes result in remarkable change in the capacity to produce TNF-α. The present invention has been completed on the basis of these findings.

Accordingly, the gist of the present invention is a method for screening genetic polymorphisms for determination of diseases wherein TNF-α participates, said method comprising detecting the presence or absence of one or more changes selected from the following nucleotide changes within the 5'-flanking region of TNF-α gene:

1) a change from cytosine (C) to thymine (T) at position −857 (position 373 in SEQ ID NO: 9),
2) a change from cytosine (C) to adenine (A) at position −863 (position 367 in SEQ ID NO: 9),
3) a change from thymine (T) to cytosine (C) at position −1031 (position 199 in SEQ ID NO: 9), and
4) respective changes corresponding thereto in the complementary strand.

In this specification, "diseases wherein TNF-A participates" means diseases wherein onset or severity of the diseases and their reactivities to treatments are affected by the amount of production of TNF-α. Included in such diseases are, for example, juvenile rheumatoid arthritis, rheumatoid arthritis, SLE naphropathy and Kawasaki disease, as well as insulin-dependent and noninsulin-dependent diabetes mellitus, and leptin-related diseases such as obesity (DIABETES, vol. 46, pp. 1468–1472 (1997)). Diseases wherein TNF-(participates also include those diseases that are related to HLA 4 or 9, for example, rheumatoid arthritis, pemphigus vulgaris, diabetes mellitus, Harada's disease, Crohn's disease, and the like.

BRIEF DESCRIPTION OF THE DRAWING

FIG. 1 shows individual differences in amount of production of TNF-A.

FIG. 2 shows polymorphisms in the promoter region of TNF-α gene.

FIG. 3 shows relationship between the amount of production of TNF-α and the polymorphisms in the promoter region of TNF-α gene.

FIG. 7 shows the base sequences (SEQ ID NOS 9, 10, and 11) of the promoter region of TNF-α gene.

MODES FOR CARRYING OUT THE INVENTION

Figure 4:
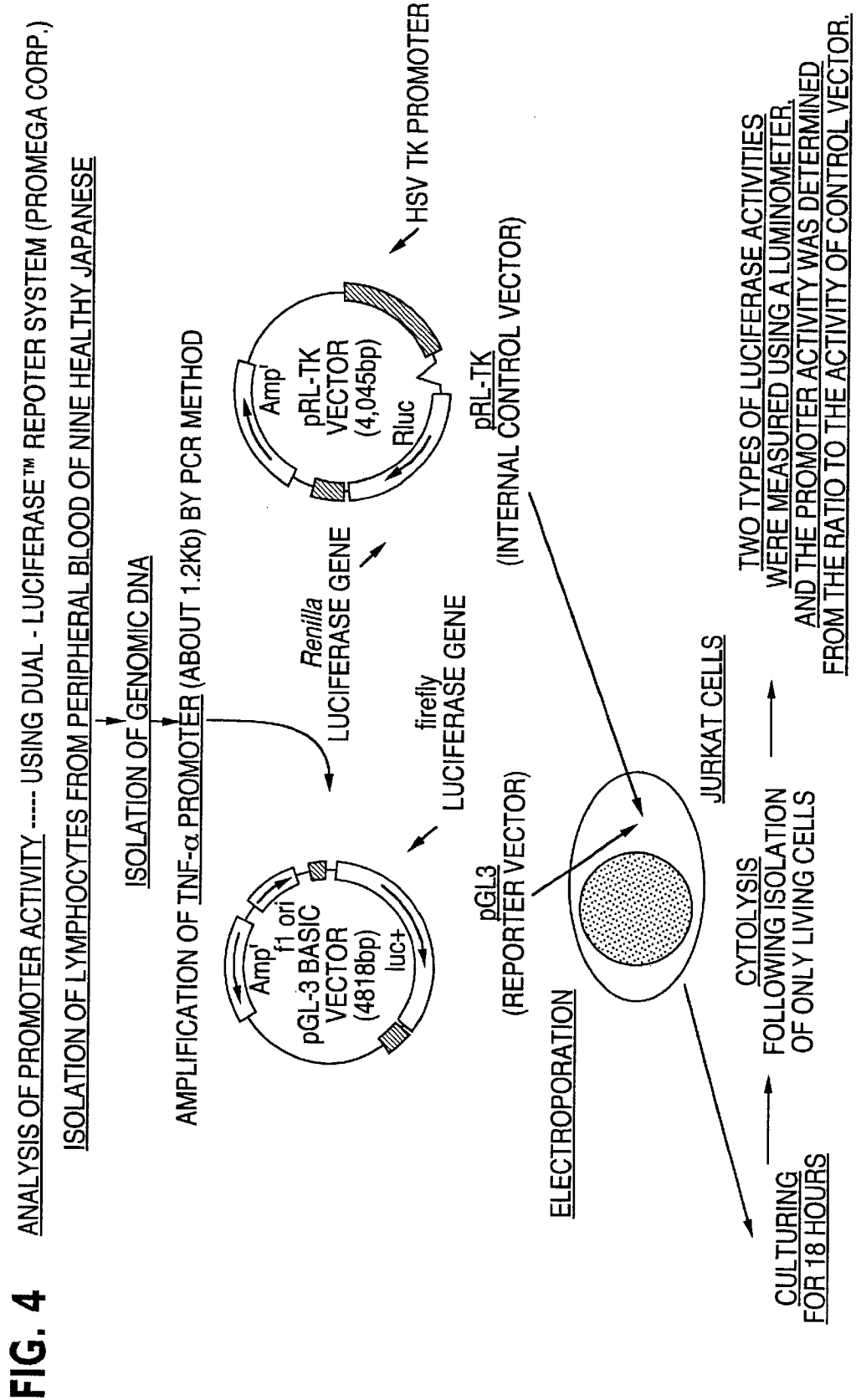
FIG. 4 shows a method for analysis of promoter activity.

Although any biopsy specimens may be used as samples from which genes are extracted, leukocytes are typically used for such purpose, and liver tissue biopsies may also be used.

After proteolysis and protein denaturation by proteinase K-SDS, the sample obtained is subjected to phenol/chloroform extraction to obtain genomic DNA (+RNA) If desired, RNA may be removed using RNase.

The genomic DNA obtained is then amplified by PCR method using the following primers:
sense primer (corresponding to the bases at positions 1–20) 5'-GCTTGTGTGTGTGTGTCTGG-3' (SEQ ID NO: 1)
   anti-sense primer (corresponding to the complementary strand of the sequence from position 1024 to position 1042) 5'-GGACACACAAGCATCAAGG-3' (SEQ ID NO: 2).

Next, the presence or absence of nucleotide changes is confirmed by the following techniques for detecting nucleic acid variations.
1) RFLP Method (Restriction Fragment Length Polymorphism)
2) PCR-SSCP Method (Single-stranded DNA Conformation Polymorphism Analysis)
3) ASO Hybridization Method (Allele Specific Oligonucleotide Hybridization)

The PCR product is dot blotted onto a support such as a nylon filter, and hybridized with an about 18-mer synthetic oligonucleotide probe having a base slequence corresponding to the site of variation to be searched (a radioisotope- or biotin-label is necessary to obtain signals) Sub sequent post-washing according to the Tm value of the probe allows detection of a single base mismatch (if there is a mismatch, the hybrid will disjoin) This is the most typical procedure as a method for detecting a particular base substitution using PCR.
4) Sequence Method The entire base sequence of the obtained region is determined to directly check the presence or absence of nucleotide changes.
5) Southern Blotting Method This is a general method wherein DNA is treated with a restriction enzyme, developed by electrophoresis, and then hybridized with a probe. Either of genomic Southern method or PCR Southern method may be used. Although the latter is the same in principle as the above (3), it has the advantage in accuracy since it provides information on mobility.
6) ARMS (Amplification Refracting Mutation System)

In PCR, after annealing of primers to DNA template, DNA polymerase synthesizes the complementary strand DNA in the direction from 5' to 3'. When a mismatch exists at the 3'-end base of the primer, the efficiency of PCR is decreased, that is, it becomes electrophoretically unobservable. ARMS takes advantages of this principle, and the presence or absence of amplified products can be detected by conducting PCR using primers having a 3'-end base complementary to the variant base to be detected.
7) DGGE (Denaturing Gradient Gel Electrophoresis)

This is a method taking advantage of the fact that, in PCR products, heteroduplexes containing a mismatch dissociates more easily than homoduplexes. Because the gel electrophoretic mobility decreases as dissociation proceeds, density gradients of urea and formamide imparted to the polyacrylamide gel, on which the PCR products are developed, further emphasize the difference, and thereby allow detection of the presence of double-stranded DNA containing a mismatch, that is, the presence of variation.
8) RNase Cleavage Method RNase A (ribonuclease) has the property of decomposing only single-stranded RNAs without decomposing double-stranded RNAs or RNA/DNA complexes. Therefore, for example, an RNA probe labeled with $^{32}p$ may be hybridized with sample DNAs denatured into the single-stranded form, treated with RNase A, and then developed by electrophoresis. Since the RNA probe hybridized with the variant form is cleaved at the site of mismatch, it can be detected as two bands.
9) Chemical Cleavage Method When "C" and IT" at the site of mismatch in a double-stranded DNA are separately modified with hydroxylamine and osmium tetraoxide, respectively, and then subjected to piperidine treatment, the sugar is cleaved. In the case that a labeled probe is used to form the double-strand, which is then subjected to the above treatment, shortening of the size of probe indicates detection of variation.
10) Ligase Method The principle underlying this method is that when two oligonucleotides are ligated with DNA ligase, the presence of mismatch with the template DNA at the site of ligation makes the ligation impossible.
i) LMGD (Ligase-mediated Gene Detection) Method One of the oligo-DNAs is labeled with $^{32}p$, while the other is labeled with biotin, and after ligation, recovery is performed by streptavidin adsorption. If these DNAs are ligated to each other (that is, if these DNAs do not mismatch), they can be detected because of the high radiation dose of $^{32}p$.
ii) LCR (Ligase Chain Reaction)

When the above-described ligation reaction is repeatedly performed using a thermostable ligase, oligo-DNAs will also anneal to DNA strands as in PCR, allowing sensitive detection of variations.

EXAMPLES

Example 1

Comparison of Capacities to Produce TNF-α

In one ml of medium (RPMI 1640+5%FCS), 1×10⁶ PBMCs (peripheral blood monocytes) isolated from one of nine healthy Japanese were suspended, stimulated with Con A(Concanavalin A; 10 □μg/ml), cultured for 20 hours at 37° C., and then the concentration of produced TNF-α in the supernatant was measured by ELISA method. The results are shown in FIG. 1.

It was found that among the nine healthy Japanese, there exist remarkable differences in amount of TNF-α production by PBMC in response to Con A stimulation.

Example 2
Analysis of Polymorphism in the TNF-α Gene Promoter Region

From PBMC isolated as in Example 1, genomic DNA was isolated, and the promoter region (about 1.3 Kbp) of TNF-α gene was amplified by PCR method. The entire base sequence was then determined by TA cloning method to analyze the presence or absence of polymorphism. The results are shown in FIGS. 2 and 7. In FIG. 7, Cases 2 X (SEQ ID NO:10) and 2 Y (SEQ ID NO:11) are aligned against the consensus sequence originally constructed (SEQ ID NO: 9).

Based on the comparison of sequences from the above nine individuals, it was found that there exist polymorphisms, which have not been reported to date, at three sites in the TNF-α gene promoter region.

Example 3
Activities of Polymorphic Promoters

These polymorphisms at positions −857, −863 and −1031 in the TNF-α gene promoter region were observed at higher frequencies in high producers of TNF-α.

Accordingly, capacities to produce TNF-α were compared between those exhibiting polymorphism at any one of positions −857, −863, and −1031 and those exhibiting no polymorphism at these positions. As a result, it was statistically demonstrated that the former has a significantly higher capacity to produce TNF-α (p value=0.05: U test of Mann-Whitney) (FIG. 3).

Next, among these polymorphisms, the promoter activities of two types of polymorphisms, one having a polymorphism at position −857 and the other having polymorphisms at positions −863 and −1031, were measured as follows using a reporter gene, and compared with each other.

The TNF-α gene promoter region was inserted into a reporter vector (PGL-3: containing firefly luciferase gene), co-transfected into a human T cell leukemia strain, Jurkat, with a control vector (pRL-TK: containing Renilla luciferase gene) by electroporation, and cultured for 18 hours. Subsequently, only living cells were separated by Ficoll density centrifugation, lysed, and then measured for their two types of luciferase activities using luminometer (FIG. 4). The promoter activity was determined from the ratio to the luciferase activity of the control vector.

The results are shown in Table 1. The TNF-α gene promoter having a polymorphism at position −857 (pGL-TNFp2X) and the promoter having polymorphisms at positions −863 and −1031 (pGL-TNFp2Y) have promoter activities about two-fold more potent than that of the conserved sequence.

TABLE 1

Relationship between polymorphisms in TNF-α promoter region and transcription activity in Cases 2, 7, and 8

| Transfection | pRL-TK | pGL activity | pRL activity | pGL/pRL (transcription activity) |
|---|---|---|---|---|
| pGL-TNFp | | | | |
| pGL-TNFp2X (Case 2X) | + | 51604 | 17094 | 3.02 |
| pGL-TNFp2Y (Case 2Y) | + | 79778 | 34474 | 2.31 |

TABLE 1-continued

Relationship between polymorphisms in TNF-α promoter region and transcription activity in Cases 2, 7, and 8

| | | | | |
|---|---|---|---|---|
| pGL-TNFp7X (Case 7X) | + | 48343 | 34828 | 1.38 |
| pGL-TNFp8X (Case 8X) | + | 45303 | 40262 | 1.13 |
| pGL-3 (vector alone) | + | 4384 | 28091 | 0.16 |

| | −1031 | −863 | −857 |
|---|---|---|---|
| Case 2X | T | C | T |
| Case 2Y | C | A | C |
| Case 7X | T | C | C |
| Case 8X | T | C | C |

Example 4
Analysis of TNF-α Gene Promoter Region Polymorphisms by ASO Hybridization Method Regarding polymorphisms at positions −857, −863, and −1031, analysis was conducted by ASO hybridization method. As in Example 2, the TNF-α gene promoter region was amplified from genomic DNA by PCR method, then dot-spotted onto a nylon filter, and fixed with an UV cross-linker. Base sequences of ASO probes were as follows.

5'-CTTAACGAAGACAGGGCC-3'
(specifically reacting with C at position −857; SEQ ID NO: 3; hereinafter referred to as H-857C)
5'-CTTAATGAAGACAGGGCC-3'
(specifically reacting with T at position −857; SEQ ID NO: 4; hereinafter referred to as H-857T)
5'-ATGGGGACCCCCCCTTAA-3'
(specifically reacting with C at position −863; SEQ ID NO: 5; hereinafter referred to as H-863C)
5'-ATGGGGACCCCCACTTAA-3'
(specifically reacting with A at position −863; SEQ ID NO: 6; hereinafter referred to as H-863A)
5'-CTGAGAAGATGAAGGAAA-3'
(specifically reacting with T at position −1031; SEQ ID NO: 7; hereinafter referred to as H-1031T)
5'-CTGAGAAGACGAAGGAAA-3'
(specifically reacting with C at position −1031; SEQ ID NO: 8; hereinafter referred to as H-1031C)

Figure 6:
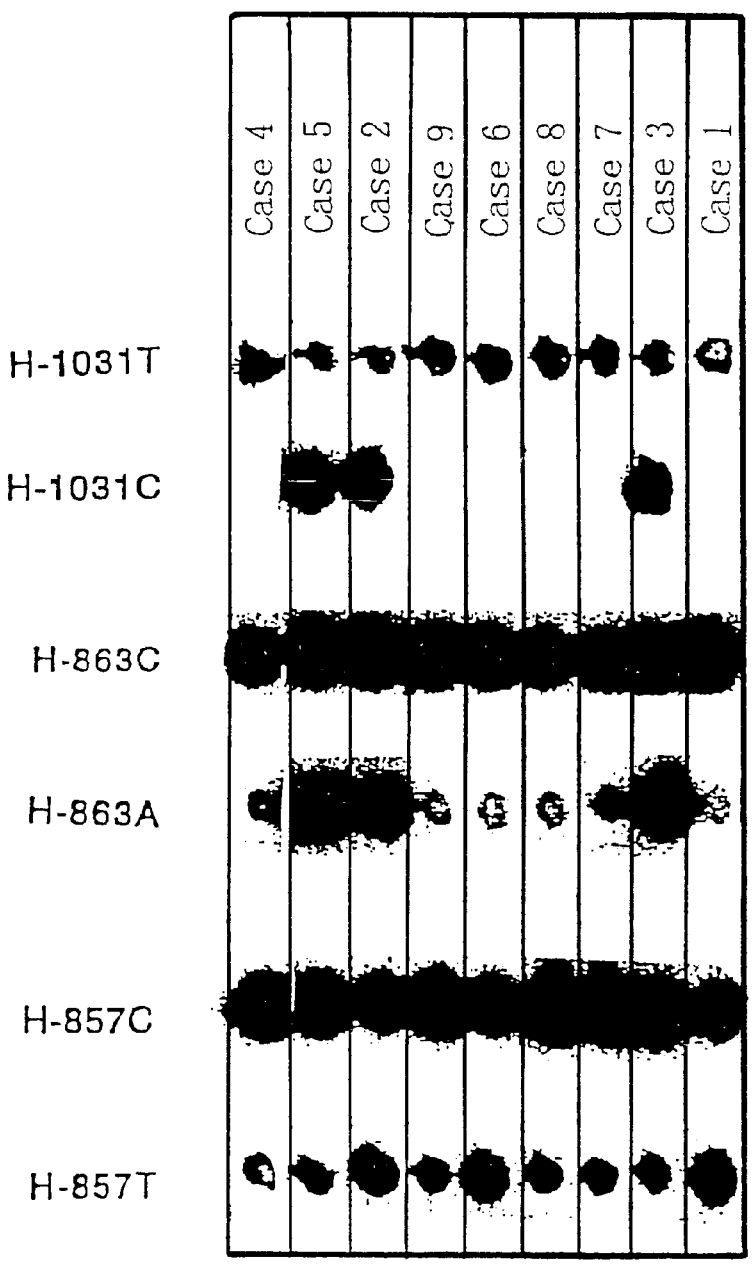
FIG. 6 is a photograph substituted for drawing, which indicates the results of electrophoresis in ASO hybridization analysis of the TNF-α promoter region.

These probes were used after end-labeling with $\gamma$-$^{32}$p-ATP. Hybridization was performed in the presence of TMAC (tetramethylammonium chloride). The results are shown in FIG. 6 and Table 2. The results obtained were completely consistent with those results of base sequences shown in FIG. 2.

TABLE 2

Confirmation of three types of polymorphisms in the TNF-α gene promoter region from nine healthy individuals by ASO-hybridization method

| Healthy Donor | Reactivity with ASO probe | | | | | |
|---|---|---|---|---|---|---|
| | H-1031T | H-1031C | H-863C | H-863A | H-857C | H-857T |
| Case 1 | + | − | + | − | + | + |
| Case 2 | + | + | + | + | + | + |
| Case 3 | + | + | + | + | + | − |
| Case 4 | + | − | + | − | + | − |
| Case 5 | + | + | + | + | + | − |
| Case 6 | + | − | + | − | + | + |
| Case 7 | + | − | + | − | + | − |

TABLE 2-continued

Confirmation of three types of polymorphisms in
the TNF-α gene promoter region from nine healthy
individuals by ASO-hybridization method

| Healthy Donor | Reactivity with ASO probe | | | | | |
|---|---|---|---|---|---|---|
| | H-1031T | H-1031C | H-863C | H-863A | H-857C | H-857T |
| Case 8 | + | − | + | − | + | − |
| Case 9 | + | − | + | − | + | − |

Example 5
TNF-α gene 5'-flanking region polymorphisms in healthy individuals

Regarding polymorphisms at positions −238, −308, −857, −863, and −1031, 575 healthy Japanese were analyzed by ASO hybridization method as in Example 4. The results are shown in Table 3.

TABLE 3

| | Nucleotide in the promoter region of TNFα | | | | Frequency (%) (healthy individuals n = 575) |
|---|---|---|---|---|---|
| | −1031 | −863 | −857 | −308 | −238 | |
| Allele A | T | C | C | G | G | 64.5 |
| Allele B | C | A | C | G | G | 14.0 |
| Allele C | C | C | C | G | G | 2.0 |
| Allele D | T | C | T | G | G | 17.7 |
| Allele E | T | C | C | A | G | 1.7 |

It can be seen that among healthy individuals, those having Allele A (an allele in which position −1031 is T, position −863 is C, position −857 is C, position −308 is G, and position −238 is G) are large in number.

Example 6
Relationship Between Juvenile Rheumatoid Arthritis and TNF-α Gene 5'-flanking Region Polymorphisms Polymorphisms at positions −857 and −1031 in 112 patients with juvenile rheumatoid arthritis (JRA) (systemic and non-systemic) were compared with those of healthy individuals (Table 4).

TABLE 4

Relationship between JRA and polymorphisms

| | −857/T+ N (%) | −857/T− N (%) | p value | odds ratio |
|---|---|---|---|---|
| healthy individuals | 186 (32.3) | 389 (67.6) | — | — |
| JRA (n = 112) | 41 (36.6) | 71 (63.4) | no significant difference | 1.208 |
| systemic (n = 51) | 26 (51.0) | 25 (49.0) | 0.011 | 2.175 |
| non-systemic (n = 61) | 15 (24.6) | 46 (75.4) | no significant difference | 0.682 |

| | −1031/C+ N (%) | −1031/C− N (%) | p value | odds ratio |
|---|---|---|---|---|
| healthy individuals | 170 (29.6) | 405 (70.4) | — | — |
| JRA (n = 112) | 43 (38.4) | 69 (61.6) | 0.0825* | 1.485 |
| systemic (n = 51) | 22 (43.1) | 29 (56.9) | 0.0635* | 2.175 |
| non-systemic (n = 61) | 21 (34.4) | 40 (65.6) | no significant difference | 1.251 |

*p = 0.043 (Fisher exact test)
**p = 0.034 (Fisher exact test)

In Table 4, "−857/T+" denotes those containing the change to T at position −857, and "−857/T−" denotes those not containing the change to T at that position (that is, those having C at that position). Similarly, "−1031/C+" denotes those containing the change to C at position −1031, and "−1031/C−" denotes those not containing the change to C at that position (that is, those having T at that position).

It can be seen that, in patients with systemic rheumatism, the ratio between −857/T+ and −857/T−, and the ratio between −1031/C+ and −1031/C− are significantly different from those of healthy individuals. This suggests that juvenile systemic rheumatoid arthritis may be diagnosed by determining the nucleotide change at position −857 or −1031.

Example 7
Relationship Between Rheumatoid Arthritis and TNF-α Gene 5'-flanking Region Polymorphisms On patients with rheumatoid arthritis (RA) (387 individuals) and healthy individuals (575 individuals), polymorphisms at position −1031, −863, −857, −308, and −238 in TNF-β gene were analyzed. The results are shown in Table 5.

TABLE 5

Genotypes of polymorphisms of 5'-flanking region of TNF-α gene and allele frequencies in RA patients and healthy donors

| position of polymorphism | −1031 | | | | | |
|---|---|---|---|---|---|---|
| | N | genotype (%) | | | allele frequency | | odds ratio[1] |
| | | TT | TC | CC | T | C | |
| RA | 387 | 260 (67.2) | 115 (29.7) | 12 (3.1) | 0.820 | 0.180 | 1.15 |
| Healthy donor | 575 | 405 (70.4) | 156 (27.3) | 14 (2.4) | 0.840 | 0.160 | — |

| position of polymorphism | −863 | | | | | |
|---|---|---|---|---|---|---|
| | N | genotype (%) | | | allele frequency | | odds ratio |
| | | CC | CA | AA | C | A | |
| RA | 387 | 270 (69.8) | 107 (27.6) | 10 (2.6) | 0.836 | 0.164 | 1.21 |
| Healthy donor | 575 | 424 (73.7) | 141 (24.5) | 10 (1.7) | 0.860 | 0.140 | — |

| position of polymorphism | −857 | | | | | |
|---|---|---|---|---|---|---|
| | N | genotype (%) | | | allele frequency | | odds ratio |
| | | CC | CT | TT | C | T | |
| RA | 387 | 199 (51.4) | 165 (42.6) | 23 (5.9) | 0.727 | 0.273 | 1.74[2] |
| Healthy donor | 575 | 389 (67.7) | 168 (29.2) | 18 (3.1) | 0.823 | 0.177 | — |

TABLE 5-continued

Genotypes of polymorphisms of 5'-flanking region of TNF-α gene and allele frequencies in RA patients and healthy donors

| position of polymorphism | | -308 | | | | |
|---|---|---|---|---|---|---|
| | | genotype (%) | | | allele frequency | odds |
| | N | GG | GA | AA | G | A | ratio |
| RA | 387 | 384 (99.2) | 3 (0.8) | 0 (0.0) | 0.996 | 0.004 | 0.22[3] |
| Healthy donor | 575 | 556 (96.7) | 18 (3.1) | 1 (0.2) | 0.983 | 0.017 | — |

| position of polymorphism | | -238 | | | | |
|---|---|---|---|---|---|---|
| | | genotype (%) | | | allele frequency | odds |
| | N | GG | GA | AA | G | A | ratio |
| RA | 387 | 376 (97.2) | 11 (2.8) | 0 (0.0) | 0.986 | 0.014 | 0.71 |
| Healthy donor | 575 | 552 (96.0) | 23 (4.0) | 0 (0.0) | 0.980 | 0.020 | — |

[1] odds ratio: odds ratios of polymorphic alleles (-1031C, -863A, -857T, -308A, or -238A) were calculated by comparing to the control healthy donors.
[2] $p < 10^{-4}$,
[3] $p = 0.014$ (by a chi-square test using Yates correction)

As shown in the above table, the proportions of the change from T to C at position -1031 (hereinafter referred to as "-1031C"), the change from C to A at position -863 (hereinafter referred to as "-863A"), the change from C to T at position -857 (hereinafter referred to as "-857T"), the change from G to A at position -308 (hereinafter referred to as "-308A"), and the change from G to A at position -238 (hereinafter referred to as "-238A) were 18.0%, 16.4%, 27.3%, 0.4%, and 1.4%, respectively, in RA patients, while they were 16.0%, 14.0%, 17.7%, 1.7%, and 2.0%, respectively, in healthy individuals. There exit statistically significant differences in proportions of -857T and -308A between RA patients and healthy individuals: when compared to healthy individuals, the proportion of those containing the change to T at position -857 is higher in RA patients, and the proportion of those containing the change from G to A at position -308 is lower in RA patients. This indicates that the polymorphisms at position -857 and -308 in TNF-α gene are involved in susceptibility to RA.

Example 8

Relationship Between Clinical Features of Rheumatoid Arthritis Patients and Polymorphisms in TNF-αGene 5'-flanking Region In rheumatoid arthritis (RA) patients, relationship between the presence or absence of -1031C, -863A or -857T and clinical features of the patient (joint score (Lansbury evaluation method), the number of swollen and purulent joints, the number of painful joints, microhematuria) was determined. The results are shown in Table 6.

TABLE 6

Study of clinical features, TNF-α gene, and HLA DRB1*0405 in RA patients

| | | -1031C | | -863A | | -857T | | DRB1*0405 | |
|---|---|---|---|---|---|---|---|---|---|
| | No.[1] | + | − | + | − | + | − | + | − |
| Joint score (mean) | 120 | 54.0[2] | 53.7 | 52.0 | 54.7 | 48.2 | 59.8 | 53.3 | 54.8 |
| Swollen and purulent joint count | 120 | 3.35[3] | 3.19 | 3.37 | 3.18 | 3.15 | 3.34 | 3.51 | 2.74 |
| Painful joint count | 120 | 9.15[4] | 7.76 | 9.00 | 7.87 | 6.89 | 9.66 | 7.49 | 9.60 |
| micro-hematuria % | 97 | 29.0[5] | 15.2 | 30.0 | 14.9 | 18.0 | 21.3 | 18.2 | 21.3 |
| HLA DRB1*0405 positive | 63 | 22.7 | 19.0 | 23.8 | 18.6 | 18.6 | 23.8 | — | — |
| HlA DRB1*0405 negative | 34 | 44.4[6] | 8.3 | 44.4[7] | 8.3 | 16.7 | 19.2 | — | — |

[1] Samples (19) of which HLA DRB1 genotypes have been defined were used in this study.
[2], [3], [4] The mean value of joint score (Lansbury evaluation method), and the mean number of swollen and purulent or painful joints are indicated. No significant difference was observed by Student's t-test between the positive and negative groups of each allele.
[5] The frequency of patients with microhematuria (1+, 2+, 3+) is indicated.
[6], [7] Odds ratio = 8.80, p = 0.034 (Fisher's exact test)

In RA patients who are negative for HLA DRB1*405, it is shown that the incidence of microhematuria is significantly higher when positive for -1031C or -863A. This suggests that polymorphisms at positions -1031 and -863 of TNF-α gene are involved in renal complications of RA.

Example 9
Relationship Between Insulin-dependent Diabetes Mellitus and TNF-α Gene 5'-flanking Region Polymorphisms On insulin-dependent diabetes mellitus (IDDM) patients (140 individuals) and healthy individuals (575 individuals), polymorphisms at position −857, −863, and −1031 in TNF-α gene were analyzed. The results are shown in Table 7.

TABLE 7

Genotypes of polymorphisms of 5'-flanking region of TNF-α gene and allele frequencies in IDDM patients and healthy donors

|  | N | −857 genotype CC | CT | TT | allele −857C | −857T | odds ratio | P | Pc |
|---|---|---|---|---|---|---|---|---|---|
| Healthy donor | 575 | 389 (67.7) | 168 (29.2) | 18 (3.1) | 946 (82.3) | 204 (17.7) | — | — | — |
| IDDM | 140 | 69 (49.3) | 61 (43.6) | 10 (7.1) | 199 (71.1) | 81 (28.9) | 1.888 | $<10^{-4}$ | $<10^{-4}$ |

|  | N | −863 genotype CC | CA | AA | allele −863C | −863A | odds ratio | P | Pc |
|---|---|---|---|---|---|---|---|---|---|
| Healthy donor | 575 | 424 (73.7) | 141 (74.5) | 10 (1.7) | 989 (86.0) | 161 (14.0) | — | — | — |
| IDDM | 140 | 82 (58.6) | 46 (32.9) | 12 (8.6) | 210 (75.0) | 70 (25.0) | 2.048 | $<10^{-5}$ | $<10^{-4}$ |

|  | N | −1031 genotype TT | TC | CC | allele −1031T | −1031C | odds ratio | P | Pc |
|---|---|---|---|---|---|---|---|---|---|
| Healthy donor | 575 | 405 (70.4) | 156 (27.1) | 14 (2.4) | 966 (84.0) | 184 (16.0) | — | — | — |
| IDDM | 140 | 81 (57.9) | 47 (33.6) | 12 (8.6) | 209 (74.6) | 71 (25.4) | 1.784 | 0.0002 | 0.0003 |

As shown in the above table, the proportions of −1031C, −863A, and −857T were 25.4%, 25.0%, and 28.9%, respectively, in IDDM patients, while they were 16.0%, 14.0%, and 17.7%, respectively, in healthy individuals. Differences in these values between the above two groups are statistically significant, indicating that polymorphisms at position −1031, −863, and −857 of TNF-α gene are involved in susceptibility to insulin-dependent diabetes mellitus.

Example 10
Relationship Between Noninsulin-dependent Diabetes Mellitus and TNF-α Gene 5'-flanking Region Polymorphisms (1)

On obese noninsulin-dependent diabetes mellitus patients (NIDDM+) (59 individuals) and healthy individuals (NIDDM−) (96 individuals), polymorphism at position −857 of TNF-α gene was analyzed. The results are shown in Table 8.

TABLE 8

Genotypes of polymorphism at position −857 of 5'-flanking region of TNF-α gene and allele frequencies in obese NIDDM vs. non-NIDDM

|  | N | −857 genotype CC | CT | TT | allele −857C | −857T | odds ratio | Pc |
|---|---|---|---|---|---|---|---|---|
| NIDDM + | 59 | 35 (59.3) | 15 (25.4) | 9 (15.3) | 85 (72.0) | 33 (28.0) | 2.37 | 0.0042 |
| NIDDM − | 96 | 69 (71.9) | 27 (28.1) | 0 (0.0) | 165 (85.9) | 27 (14.1) |  |  |

As shown in the above table, the proportion of −857T was 28.0% in DM patients, whereas it was 14.0% in healthy individuals, and there was statistically significant difference between these values.

This indicates that, among obese people, the polymorphism at position −857 of TNF-α gene is involved in diabetes mellitus.

Example 11
Relationship Between Noninsulin-dependent Diabetes Mellitus and TNF-α Gene 5'-flanking Region Polymorphisms (2)

On nonobese noninsulin-dependent diabetes mellitus patients (NIDDM+) (154 individuals) and healthy individuals (NIDDM−) (195 individuals), polymorphisms at positions −1031 and −863 of TNF-α gene were analyzed. The results are shown in Table 9.

TABLE 9

Genotypes of polymorphisms at positions −863 and −1031 of 5'-flanking region of TNF-α gene and allele frequencies in nonobese NIDDM vs. non-NIDDM

| | N | −863 genotype | | | allele | | odds ratio | Pc |
|---|---|---|---|---|---|---|---|---|
| | | CC | CA | AA | −863C | −863A | | |
| NIDDM + | 154 | 125 (81.2) | 25 (16.2) | 4 (2.6) | 275 (89.3) | 33 (10.7) | 0.57 | 0.0165 |
| NIDDM − | 195 | 134 (68.7) | 54 (27.7) | 7 (3.6) | 322 (82.6) | 68 (17.4) | | |

| | N | −1031 genotype | | | allele | | odds ratio | Pc |
|---|---|---|---|---|---|---|---|---|
| | | TT | TC | CC | −1031T | −1031C | | |
| NIDDM + | 154 | 121 (78.6) | 29 (18.8) | 4 (2.6) | 271 (88.0) | 37 (12.6) | 0.6030 | 0.0261 |
| NIDDM − | 195 | 130 (66.7) | 58 (29.7) | 7 (3.6) | 318 (81.5) | 72 (18.5) | | |

As shown in the above table, the proportions of −1031C and −863A were 12.0% and 10.7%, respectively, in NIDDM patients, whereas they were 18.5% and 17.4%, respectively, in healthy individuals. The differences between these values are statistically significant.

This indicates that, among non-obese people, polymorphisms at positions −1031 and −863 of TNF-α gene are involved in diabetes mellitus.

Example 12
Relationship Between DRB1 Allele of HLA and TNF-α Gene 5'-flanking Region Polymorphisms It is known that there exist many polymorphisms in DRB1 of human leukocyte antigen (HLA). Accordingly, relationship between DRB1 alleles of HLA and polymorphisms in TNF-α gene 5'-flanking region according to the present invention was determined.

TABLE 10

| | Correlation between DRB1 0901 allele and allele B | | | | | | |
|---|---|---|---|---|---|---|---|
| | DRB1 | | | | | | odds ratio |
| | 0901 + | 0901 − | Δ | t | Hf | p value* | |
| allele B+ | 63 | 58 | 0.0386 | 5.279 | 0.0636 | <10⁻⁸ | 3.513 |
| allele B− | 78 | 249 | | | | | |

| | Correlation between DRB1 0405 allele and allele D | | | | | | |
|---|---|---|---|---|---|---|---|
| | DRB1 | | | | | | odds ratio |
| | 0405 + | 0405 − | Δ | t | Hf | p value* | |
| allele D+ | 69 | 76 | 0.0508 | 6.937 | 0.0741 | <10⁻¹⁰ | 5.947 |
| allele D− | 40 | 262 | | | | | |

*Statistical significance was evaluated by the chi-square test.

In Table 10, "0901+" refers to DPB1 0901 allele, and "0901−" refers to those alleles that are not DPB1 0901 allele. Similarly, "0405+" refers to DPB1 0405 allele, while "0405−" refers to those alleles that are not DPB1 0405 allele.

Furthermore, "allele B+" refers to allele B, and "allele B−" refers to those alleles that are not allele B (i.e., allele A, C, D, or E). Similarly, "allele D+" refers to allele D, while "allele D−" refers to those alleles that are not allele D (i.e., allele A, B, C, or E). For alleles A, B, C, D, and E, see Example 5.

Figure 5:
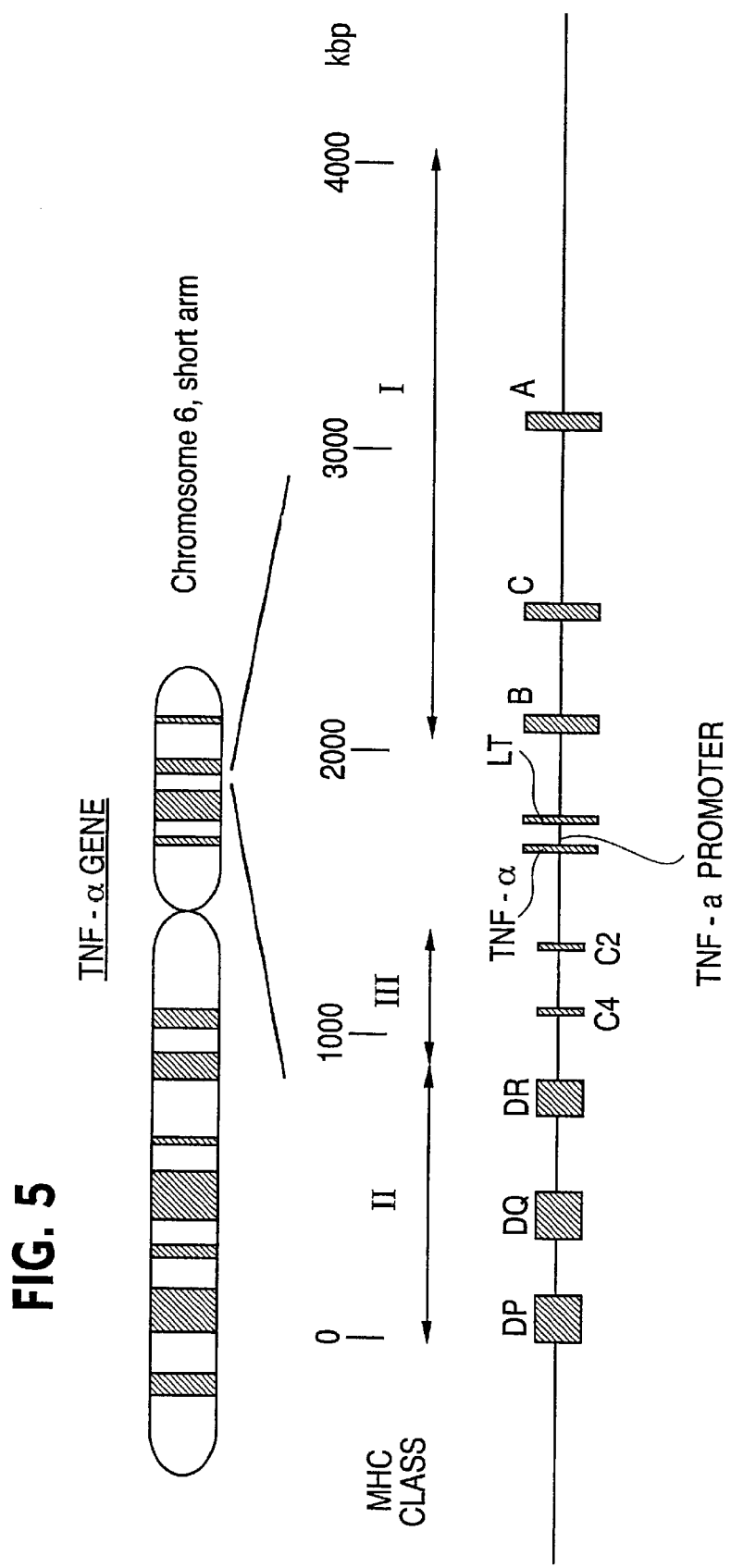
FIG. 5 shows the position of TNF-α gene on the chromosome.

As apparent from the table, strong correlations are observed between HLA DRB1 0901− and allele B−, and between HLA DRB1 0405− and allele D−. Since the 5'-flanking region of TNF-α is located between HLA class I and class II on the chromosome, as shown in FIG. 5, there is a possibility that HLA and TNF-α promoter are linked to each other.

On the other hand, relationship between HLA and susceptibility to diseases has previously been pointed out ("Ika-Meneki-Gaku" revised 4th edition, p. 107, Kikuchi Hirokichi Ed., Nanko-Do). For example, those having HLA DRB1 405 are said to have increased susceptibility to rheumatoid arthritis, pemphigus vulgaris, diabetes mellitus, Harada's disease, Crohn's disease, and the like. Accordingly, this suggests a possibility that prior diagnoses for these diseases may be conducted by determining polymorphisms in TNF-α gene 5'-flanking region.

As described above, according to the present method of screening for disease genetic polymorphisms wherein TNF-α participates, by measuring nucleotide changes at particular positions within TNF-α gene 5'-flanking region of a given individual, one can determine the capacity of the individual to produce TNF-α, and thereby conduct prior diagnosis or determination of prognosis for diseases wherein TNF-α participates.

What is claimed is:

1. A method for screening for insulin-dependent diabetes mellitus, which comprises detecting the presence of one or more changes selected from the following nucleotide changes within the 5'-flanking region of human TNF-α gene:
- (a) a change from cystine (C) to thymine (T) at position −857
- (b) a change from cytosine (C) to adenine (A) at position −863
- (c) a change from thymine (T) to cytosine (C) at position −1031, and
- (d) a change in the complementary strand which corresponds to the change in (a), (b), or (c) wherein the presence of one or more changes within the 5'-flanking region indicates susceptibility to IDDM.

2. A method for screening for non-insulin-dependent diabetes mellitus (NIDDM), which comprises detecting the presence of one or more changes selected from the following nucleotide changes within the 5'-flanking region of human TNF-α gene:
- (a) a change from cytosine (C) to thymine (T) at position −857
- (b) a change from cytosine (C) to adenine (A) at position −863
- (c) a change from thymine (T) to cytosine (C) at position −1031, and
- (d) a change in the complementary strand which corresponds to the change in (a), (b), or (c);

provided that the detection of a change at position −857 is to screen for NIDDM in obese patients, and the detection of changes at positions −863 and −1031 are to screen for NIDDM in non-obese patients wherein the presence of one or more changes within the 5'-flanking region indicates susceptibility to NIDDM.

3. A method for screening for rheumatoid arthritis, which comprises detecting the presence of a change from cytosine (C) to thymine (T) at position −857 within the 5'-flanking region of human TNF-α gene or a change corresponding thereto in the complementary strand wherein the presence of the change within the 5'-flanking region indicates susceptibility to rheumatoid arthritis.

4. A method for screening for juvenile rheumatoid arthritis, which comprises detecting the presence of one or more changes selected from the following nucleotide changes within the 5'-flanking region of human TNF-α gene:
- (a) a change from cytosine (C) to thymine (T) at position −857
- (b) a change from thymine (T) to cytosine (C) at position −1031, and
- (c) a change in the complementary strand which corresponds to the change in (a) or (b) wherein the presence of one or more changes within the 5'-flanking region indicates susceptibility to juvenile rheumatoid arthritis.

\* \* \* \* \*